United States Patent [19]

Franke

[11] 3,957,928

[45] *May 18, 1976

[54] S-AMMONIUM-O-HYDROCARBYL-N-ACYL PHOSPHORAMIDOTHIOATE SALT PRODUCTION AND REACTION WITH ALKYLATING AGENT

[75] Inventor: Hans G. Franke, Orinda, Calif.

[73] Assignee: Chevron Research Company, San Francisco, Calif.

[ * ] Notice: The portion of the term of this patent subsequent to Aug. 27, 1991, has been disclaimed.

[22] Filed: June 17, 1974

[21] Appl. No.: 479,973

Related U.S. Application Data

[63] Continuation-in-part of Ser. No. 317,479, Dec. 21, 1972, Pat. No. 3,832,425.

[52] U.S. Cl............................ 260/978; 260/979; 260/987; 260/959; 424/220
[51] Int. Cl.$^2$...................... C07F 9/32; A01N 9/36
[58] Field of Search...................... 260/987, 979, 978

*Primary Examiner*—Anton H. Sutto
*Attorney, Agent, or Firm*—George F. Magdeburger; John Stoner, Jr.; Raymond Owyang

[57] ABSTRACT

S-ammonium salts of O-hydrocarbyl-N-acylphosphoroamidothioates are prepared by reacting an O,O-dihydrocarbyl-N-acyl-phosphoroamidothioate with an ammonium sulfide or polysulfide in a liquid ammonia reaction medium.

12 Claims, No Drawings

1

S-AMMONIUM-O-HYDROCARBYL-N-ACYL PHOSPHORAMIDOTHIOATE SALT PRODUCTION AND REACTION WITH ALKYLATING AGENT

RELATED APPLICATION

This application is a continuation-in-part of application Ser. No. 317,479, filed Dec. 21, 1972, now U.S. Pat. No. 3,832,425, the disclosure of which is incorporated by reference.

BACKGROUND OF THE INVENTION

U.S. Pat. No. 3,676,555, issued to G. Schrader et al, discloses that compounds having the general formula (I)

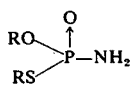
(I)

wherein R is alkyl are excellent insecticides. These compounds are prepared from S-sodium-O-alkylphosphoroamidothioate by reaction with a methylating agent such as methyl iodide. The sodium salt, in turn, is obtained by the reaction of sodium hydroxide with an O,O-dialkylphosphoroamidothioate as illustrated in the following equation (1):

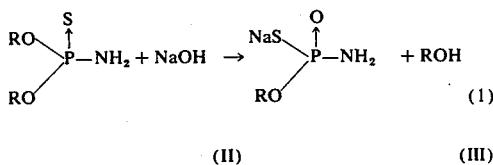

(II)        (III)

wherein R is alkyl.

Unfortunately the insecticides of formula (I) have relatively high mammalian toxicity and are therefore of limited use. U.S. Pat. No. 3,716,600, issued Feb. 13, 1973, to P. S. Magee, discloses that N-acylated derivatives, e.g., N-acetyl, of the compounds of formula (I) are of essentially equal insecticidal activity but are significantly less toxic to mammals. However, it has been found by experimentation that preparation of the new and safer insecticides of U.S. Pat. No. 3,716,600 from the sodium salt of the corresponding N-acylated phosphoroamidothioate was not possible because the sodium salt would not form upon the reaction of an O,O-dialkyl-N-acylphosphoroamidothioate with sodium hydroxide. Under mild conditions only starting material was recovered; and under more severe conditions, degradation occurred without the formation of the desired sodium salt.

DESCRIPTION OF THE PRIOR ART

U.S. Pat. No. 3,662,034, issued May 9, 1972, to A. A. Oswald et al, discloses the dealkylation of S-allylic and S-vinylic O,O'-dialkyldithiophosphates with metal sulfides or ammonia to form the corresponding S-salts.

SUMMARY OF THE INVENTION

It has now been found that an S-ammonium salt is formed from an O,O-dihydrocarbyl-N-acylphosphoroamidothioate by reaction with an ammonium sulfide or polysulfide in a liquid ammonia reaction medium.

DESCRIPTION OF THE INVENTION

The O,O-dihydrocarbyl-N-acylphosphoroamidothioate Reactant

The O,O-dihydrocarbyl-N-acylphosphoroamidothioate reactant employed in the process of the invention is represented by the following formula (IV):

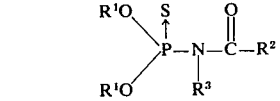
(IV)

wherein $R^1$ is alkyl, alkenyl or alkynyl of up to 6 carbon atoms, $R^2$ has up to 18 carbon atoms and is hydrogen, alkyl, alkenyl, phenyl, phenylalkyl or alkphenyl substituted with up to 3 fluorine, chlorine or bromine atoms or with up to 1 alkoxy or alkylthio of 1 to 4 carbon atoms, and $R^3$ is hydrogen or alkyl or 1 to 6 carbon atoms.

Representative alkyl groups which $R^1$ and $R^3$ may represent include methyl, ethyl, propyl, isopropyl, butyl, sec-pentyl and hexyl. Prepresentative $R^1$ alkenyl groups of 2 to 6 carbon atoms include vinyl, allyl, 2-butenyl, 3-butenyl, 2-hexenyl, 5-hexenyl, etc. Representative $R^1$ alkynyl groups of 3 to 6 carbon atoms include 2-propynyl, 2-butynyl, 3-butynyl, 3-pentynyl, 5-hexynyl, etc. The $R^1$ groups of formula (IV) may be the same or different The preferred $R^1$ group is alkyl of 1 to 3 carbon atoms, especially methyl. The preferred $R^3$ group is hydrogen.

Representative alkyl $R^2$ groups are methyl, ethyl, propyl, isopropyl, sec-butyl, pentyl, hexyl, octyl, decyl, dodecyl, tridecyl, pentadecyl, octadecyl, etc. Representative alkenyl $R^2$ groups are allyl, 2-butenyl, 5-hexenyl, 9-decenyl, 14-pentadecenyl, etc. Representative phenylalkyl $R^2$ groups are benzyl, 2-phenylethyl, 3-(o-tolyl)propyl, 4-phenylhexyl, 6-(o-tolyl)hexyl, etc. Representative alkphenyl $R^2$ groups are o-tolyl, p-tolyl, 2,4-dimethylphenyl, 3,5-diisopropylphenyl, 4-t-butylphenyl, etc.

Representative halo-, alkoxy- and alkylthio-substituted $R^2$ groups include haloalkyl groups such as fluoromethyl, chloromethyl, dichloromethyl, trichloromethyl, tetrachloroethyl, 3-chloropropyl, 4-bromobutyl, 10-chlorodecyl, 14-bromotetradecyl, etc.; haloalkenyl such as trichlorovinyl, 2,2-difluorovinyl, 2-bromo-9-decenyl, etc.; haloaryl groups such as 4-chlorophenyl, 2,4-difluorophenyl, 3,5-dibromophenyl, 4-chlorobenzyl, 2-chloro-4-methylphenyl, etc.; alkoxyalkyl groups such as methoxymethyl, ethoxymethyl, 2-ethoxyethyl, 4-butoxybutyl, etc.; alkoxyalkenyl such as 4-methoxy-2-butenyl, 5-ethoxy-3-pentenyl, etc.; alkoxyaryl such as 4-methoxyphenyl, 2-methoxy-4-methylphenyl, 3-propoxyphenyl, 2-(2-methoxyphenyl)ethyl, etc.; alkylthioalkyl such as methylthiomethyl, ethylthiomethyl, 2-ethylthioethyl, 5-pentylthiopentyl, etc.; alkylthioalkenyl such as 4-methylthio-2-butenyl, 4-ethylthio-3-hexenyl, etc.; alkylthioaryl such as 4-methylthiophenyl, 2-ethylthiobenzyl, 3-methyl-4-methylthiophenyl, 4-(2-methylthiophenyl)butyl, etc.

Preferred $R^2$ groups have up to 12 carbon atoms. More preferred $R^2$ groups are alkyl of 1 to 12 carbon atoms and alkoxyalkyl of 2 to 12 carbon atoms. The most preferred $R^2$ groups are alkyl of 1 to 6 carbon atoms, especially methyl.

The compounds of Formula (I) may be prepared by acylating an O,O-dhydrocarbylphosphoroamidothioate with an appropriate acylating agent, e.g., an acid halide (VI) or acid anhydride (VIII), as depicted in the following equation (2):

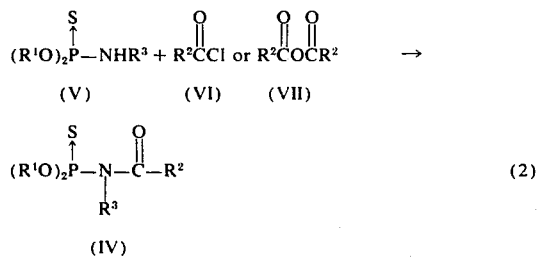

wherein $R^1$, $R^2$ and $R^3$ have the same significance as previously defined.

The acylation reaction (2) is usually carried out at about 0°-60°C. in the presence of solvent such as dichloromethane, chloroform, tetrahydrofuran and benzene. Pressure is not critical in this reaction. For convenience, atmospheric or autogenous pressure may be used. Under normal conditions, stoichiometric proportions or a slight excess of the acylating agent (VI or VII) will be used. The acylation reaction will usually take 2 to 24 hours to reach completion. The product (IV) may be purified by conventional techniques such as extraction, crystallization, chromatography, etc.

The O,O-dihydrocarbylphosphoroamidothioate compounds (V) used to prepare the N-acylphosphoroamidothioate compound (IV) may be prepared by the following reactions:

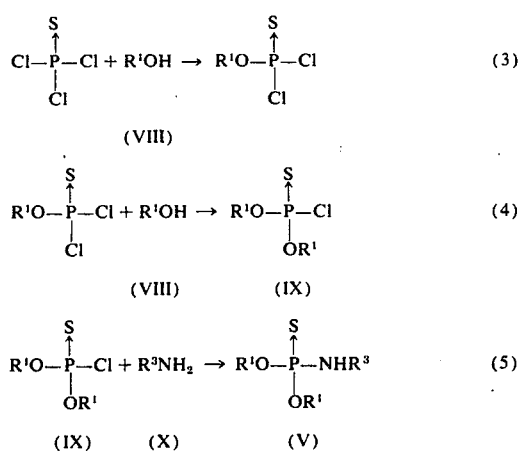

wherein $R^1$ and $R^3$ have the same significance as previously defined.

The first two reactions [equations (3)-(4)] of the synthesis involve the addition of 2 mols of the alcohol (VIII) to 1 mol of phosphorus thiochloride (PSC13) (if both $R^1$ groups are the same, a single reaction can be carried out). These reactions are preferably carried out in the presence of a weak base, such as the organic amines, for example pyridine, dimethylaniline, triethylamine, etc. The base is preferably present in an amount at least equal to the mols of alcohol. An inert organic solvent, such as diethyl ether, tetrahydrofuran, dioxane, dichloromethane, etc., may be present. The reaction temperatures are generally in the range 0° to 15°C., preferably 0° to 5°C. The reaction time necessary to complete the addition of the alcohol (VIII) to the phosphorus thiochloride will range from about 1 to 10 hours. The O,O-dihydrocarbylphosphorochloridothioate product (IX) can be purified by distillation, if desired.

The third reaction [equation (5)] of the synthesis is carried out by reacting excess (e.g., 2 molar equivalents) of gaseous ammonia or the amine (X) with the O,O-dihydrocarbylphosphorochloridothioate (IX). The reaction is generally carried out in an inert organic solvent, such as benzene, toluene, xylene and the like, at temperatures in the range 10 -75°C. Completion of the reaction is indicated by cessation of ammonium chloride or amine hydrochloride precipitation. Following the reaction, the product (V) can be isolated by conventional methods such as filtration, extraction, distillation, chromatography, etc.

The Sulfide and Polysulfide Reactants

Ammonium sulfide and polysulfide, e.g. $(NH_4)\ 2S_x$ wherein $x$ is 1 to 5, of reasonable purity are suitably employed in the process of the invention. Since the process of the invention is conducted in liquid ammonia and under essentially anhydrous conditions (i.e., the amount of water is generally less than 1 to 3% by weight, based on the weight of the total reaction mixture), the ammonium sulfide and polysulfide reactants are most conveniently prepared in liquid ammonia solution. For example, ammonium sulfide can be prepared by reacting hydrogen sulfide and excess ammonia, and ammonium polysulfide can be prepared by reacting hydrogen sulfide, sulfur and excess ammonia, as disclosed by Mellor, "Inorganic and Theoretical Chemistry," Vol. VIII, Supp. 1, p. 471, 1964.

The Reaction Conditions

The process of the invention is conducted in the liquid phase in a liquid ammonia reaction medium. Generally, from about 2 to 200 mols of liquid ammonia per mol of ammonium sulfide or polysulfide are satisfactorily employed, although amounts from about 5 to 100 mols of liquid ammonia per mol of ammonium sulfide or polysulfide are preferred. Organic co-solvents are suitably employed with the liquid ammonia. Suitable organic co-solvents include oxygenated hydrocarbons such as alkanols of 1 to 6 carbon atoms, e.g., methanol, ethanol, isopropanol, butanol, hexanol, etc.; dialkyl ketones of up to 8 carbon atoms, e.g., acetone, methylethylketone, etc.; acyclic alkyl ethers, e.g., dimethyl ether, dibutyl ether, dimethoxyethane, diethylene glycol dimethyl ether, etc.; and cycloalkyl ethers, e.g., dioxane, tetrahydrofuran and tetrahydropyran. Other suitable organic co-solvents include nitriles such as acetonitrile and propionitrile; dialkylamides such as dimethylformamide, dialkylsulfoxides such as dimethylsulfoxide and chlorinated hydrocarbons such as chloroform and dichloromethane. Suitable mixtures of liquid ammonia and organic co-solvent vary by volume, from about 10% co-solvent to 90% co-solvent and from about 10% liquid ammonia to 90% liquid ammonia.

The temperature of the reaction may vary from about −35°C. to 75°C., preferably from 0° to 75°C. Pressure is not critical, so long as the reaction mixture is maintained substantially in a non-gaseous phase. Typical pressures vary from 1 to 10 atmospheres. The time of reaction varies with the temperature. In general, the reaction is complete within 10 hours, more usually within 5 hours or less.

The molar ratio of ammonium sulfide or polysulfide to N-acylphosphoroamidothioate varies from about 1:2 to 10:1, preferably from about 1:2 to 2:1.

The precise method of contacting the reactants employed in the process is not critical. In a preferred modification, hydrogen sulfide is added to excess liquid ammonia to form a solution of the ammonium sulfide reactant in liquid ammonia, and then the N-acylphosphoroamidothioate is added neat or in an organic solvent to the solution of ammonium sulfide. The S-ammonium N-acylphosphoroamidothioate salt product is sometimes soluble in the reaction medium and may be used for further reactions without separation. However, the product usually precipitates as a solid crystalline material which may be isolated by filtration, or by decantation or evaporation of the reaction solvent. The solid product can be purified by washing with a liquid or by crystallization from an appropriate solvent such as acetone, ethanol, etc.

The Metal and Ammonium Phosphoroamidothioate Salts

The S-ammonium salts produced by the process of the invention are represented by Formula (XII)

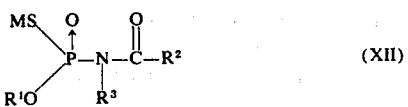

(XII)

wherein $R^1$, $R^2$ and $R^3$ have the same significance as previously defined.

Illustrative S-ammonium salts of Formula (XII) are:
S-ammonium-N-acetoyl-O-methylphosphoroamidothioate,
S-ammonium-N-crotonoyl-O-ethylphosphoroamidothioate,
S-ammonium-N-trichloroacetyl-N-methyl-O-propylphosphoroamidothioate,
S-ammonium-N-methoxyacetyl-O-methylphosphoroamidothioate,
S-ammonium-N-4-chlorocrotonoyl-O-butylphosphoroamidothioate,
S-ammonium-N-4-alkoxybenzoyl-O-methylphosphoroamidothioate,
S-ammonium-N-3-phenylpropionyl-O-methylphosphoroamidothioate,
S-ammonium-N-acetyl-O-allylphosphoroamidothioate,
S-ammonium-N-acetyl-O-propargylphosphoroamidothioate,
S-ammonium-N-acetyl-N-isopropyl-O-allylphosphoroamidothioate,
S-ammonium-N-methoxyacetyl-O-allylphosphoroamidothioate,
S-ammonium-N-methylthioacetyl-O-methylphosphoroamidothioate, and
S-ammonium-N-dichloroacetyl-O-methylphosphoroamidothioate.

The ammonium salts prepared by the process of this invention are useful intermediates for the preparation of O-hydrocarbyl-S-alkyl- or alkenyl-N-acylphosphoroamidothioates. They are especially useful in the preparation of compounds having different groups attached to the sulfur and oxygen atoms. These derivatives are prepared by reacting the salt with an alkylating agent. Suitable alkylating agents include the alkyl and alkenyl halides of up to 10 carbon atoms, such as methyl iodide, ethyl bromide, allyl chloride, hexyl bromide, crotyl chloride, benzyl chloride, propargyl bromide, isopropyl iodide, etcl; the dialkyl and dialkenyl sulfates of up to 10 carbon atoms, such as dimethyl sulfate, diethyl sulfate, diallylsulfate, etc.; and the alkyl and alkenyl aryl- or alkenesulfonates, such as methyl p-toluene sulfonate, ethyl 2,4-xylenesulfonate, allyl p-toluenesulfonate, methyl methanesulfonate, allyl methanesulfonate, etc. The preferred alkylating agents are the dialkyl sulfates, especially dimethyl sulfate.

Alkylation is effected by mixing the S-salts of the N-acylated phosphoroamidothioates and the alkylating agent in an inert solvent or an excess of liquid alkylating agent at temperatures in the range 0°–80°C. Suitable solvents are the halogenated hydrocarbons such as dichloromethane, chloroform, tetrachloroethane, or acetonitrile, acetone, methanol, etc. The preferred solvent is water.

The following examples illustrate the variations in the process of making S-salts on N-acylphosphoroamidothioates.

EXAMPLES

Example 1

A 100-ml sample of ammonia was liquefied in a 200-ml flask immersed in a dry ice/acetone bath. Into the liquid ammonia was bubbled 2.5 g (0.075 mol) hydrogen sulfide gas. To the resulting solution of ammonium sulfide was added 9.2 g (0.05 mol) O,O-dimethyl-N-acetylphosphoroamidothioate. The reaction mixture was warmed to 10°C. and maintained at this temperature for 3 hours. The liquid ammonia was allowed to evaporate by letting the reaction mixture stand overnight at 25°C. The reaction product mixture was slurried with acetonitrile and filtered to give 9.1 g (98% yield) of S-ammonium-O-methyl-N-acetylphosphoroamidothioate, as a white solid.

Example 2

A 4.1-g (0.12 mol) sample of hydrogen sulfide was bubbled into 100 ml of liquid ammonia at −30°C. A solution of 18.3 g (0.1 mol) O,O-dimethyl-N-acetyl phosphoroamidothioate in 18 g methylene dichloride was added slowly to the resulting ammonium sulfide/-liquid ammonia solution. The liquid ammonia was allowed to slowly boil off by letting the reaction mixture warm to about 10°C. After standing overnight at about 25°C., the reaction mixture became a hard, dry cake. The cake was ground up in a mortar, slurried with acetonitrile and filtered to give 17.3 g (88% yield) of the S-ammonium-O-methyl-N-acetylphosphoroamidothioate, as a white solid.

Example 3

A solution of 8.4 g (0.045 mol) S-ammonium-O-methyl-N-acetylphosphoroamidothioate, prepared by a procedure similar to that of Example 2, and 6.3 g (0.05 mol) dimethyl sulfate in 1.25 ml ethanol and 37.5 ml dichloromethane was refluxed for 3½ hours and then stirred at about 25°C. for about 16 hours. The reaction mixture was filtered and evaporated under reduced pressure to give 8.1 g (98%) O,S-dimethyl-N-acetyl-phosphoroamidothioate (a commercial insecticide).

What is claimed is:
1. A process for preparing S-ammonium salts of N-acylphosphoroamidothioates which comprises reacting an O,O-dihydrocarbyl-N-acylphosphoroamidothioate of the formula

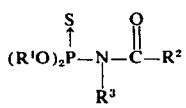

wherein $R^1$ individually is alkyl, alkenyl, or alkynyl of up to 6 carbon atoms, $R^2$ has up to 18 carbon atoms and is hydrogen, alkyl, alkenyl, phenyl, aralkyl or alkaryl substituted with up to 3 fluorine, chlorine or bromine atoms or with up to 1 alkoxy or alkylthio of 1 to 4 carbon atoms, and $R^3$ is hydrogen or alkyl of 1 to 6 carbon atoms, with an ammonium sulfide or polysulfide in liquid phase in liquid ammonia at a temperature of about −35°C. to 75°C.

2. The process of claim 1 wherein $R^1$ is alkyl, $R^2$ is alkyl of 1 to 12 carbon atoms and $R^3$ is hydrogen.

3. The process of claim 2 wherein $R^2$ is alkyl of 1 to 6 carbon atoms.

4. The process of claim 3 wherein $R^1$ and $R^2$ are methyl.

5. The process of claim 4 wherein the ammonium sulfide is generated in situ from hydrogen sulfide and liquid ammonia.

6. The process of claim 5 wherein the molar ratio of ammonium sulfide to N-acylphosphoroamidothioate varies from about 1:2 to 2:1.

7. The process of claim 2 wherein an organic co-solvent is employed.

8. The process of claim 2 wherein the ammonium sulfide is generated in situ from hydrogen sulfide and liquid ammonia.

9. A process for producing an O-hydrocarbyl-S-hydrocarbyl-N-acylphosphoroamidothioate which comprises:
1. reacting an N-acylphosphoroamidothioate of the formula

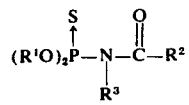

wherein $R^1$, $R^2$ and $R^3$ are as defined in claim 1, and an ammonium sulfide or polysulfide in liquid phase in liquid ammonia at a temperature of aout −35°C. to 75°C. to produce an S-ammonium salt of the N-acylphosphoroamidothioate;
2. evaporating the liquid ammonia; and
3. reacting the resulting S-ammonium salt with an alkylating agent to produce the O-hydrocarbyl-S-hydrocarbyl-N-acylphosphoroamidothioate.

10. The process of claim 9 wherein $R^1$ and $R^2$ are methyl and $R^3$ is hydrogen.

11. The process of claim 9 wherein the alkylating agent is dimethyl sulfate.

12. The process of claim 9 wherein ammonium sulfide is generated in situ from hydrogen sulfide and liquid ammonia.

* * * * *